(12) United States Patent
Balz et al.

(10) Patent No.: US 10,514,367 B2
(45) Date of Patent: Dec. 24, 2019

(54) REAL TIME INDICATOR FOR QUATERNARY AMMONIUM COMPOUND CONCENTRATION

(71) Applicant: Ecolab USA Inc., St. Paul, MN (US)

(72) Inventors: Eric Balz, Stillwater, MN (US); Kim R. Smith, Woodbury, MN (US); Erik C. Olson, Savage, MN (US); Sherri Tischler, Inver Grove Heights, MN (US)

(73) Assignee: Ecolab USA Inc., St. Paul, MN (US)

( * ) Notice: Subject to any disclaimer, the term of this patent is extended or adjusted under 35 U.S.C. 154(b) by 580 days.

(21) Appl. No.: 14/835,096

(22) Filed: Aug. 25, 2015

(65) Prior Publication Data

US 2015/0362466 A1 Dec. 17, 2015

Related U.S. Application Data

(63) Continuation of application No. 13/605,862, filed on Sep. 6, 2012, now Pat. No. 9,144,620.

(Continued)

(51) Int. Cl.
*G01N 31/22* (2006.01)
*A61L 2/28* (2006.01)
(Continued)

(52) U.S. Cl.
CPC .............. *G01N 31/22* (2013.01); *A61L 2/28* (2013.01); *B65D 79/02* (2013.01); *B65D 81/28* (2013.01); *G01N 31/229* (2013.01); *B65D 2203/02* (2013.01); *B65D 2203/12* (2013.01); *Y10T 436/173845* (2015.01)

(58) Field of Classification Search
CPC ........ G01N 31/22; G01N 31/229; A61L 2/28; B65D 79/02; B65D 81/28; B65D 2203/02; B65D 2203/12; Y10T 436/173845
See application file for complete search history.

(56) References Cited

U.S. PATENT DOCUMENTS

| | | | |
|---|---|---|---|
| 2,599,697 A | 6/1952 | Conklin | |
| 3,067,015 A * | 12/1962 | Lawdermilt | .............. 116/206 |

(Continued)

FOREIGN PATENT DOCUMENTS

| | | |
|---|---|---|
| EP | 890835 A2 | 7/1997 |
| EP | 1755536 B1 | 6/2005 |

(Continued)

OTHER PUBLICATIONS

Lowry, J. B. "Direct spectrophotometric assay of quaternary ammonium compounds using bromthymol blue." Journal of pharmaceutical sciences 68.1 (1979): 110-111.*

*Primary Examiner* — Robert J Eom
(74) *Attorney, Agent, or Firm* — Merchant & Gould P.C.

(57) ABSTRACT

The present disclosure generally relates to a color indicator that signals when the concentration of an antimicrobial solution changes. In some embodiments, the color indicator is specific for changes in the concentration of an antimicrobial quaternary ammonium compound in an antimicrobial solution. The color indicator can be incorporated into a variety of articles including towels, labels, containers, buckets, trays, sinks, spray bottles, liners for containers, buckets, sinks, or spray bottles, indictor wands or strips, and test kits.

15 Claims, 1 Drawing Sheet

Color Change of Dyes with Addition of Quaternary Ammonium Compound Under Various pH Conditions

| | Initial Screen | | Effect of pH on Screening Solutions (diluted to 75% original conc.) | | | | | |
|---|---|---|---|---|---|---|---|---|
| | pH 7-8 | | no quat | | | with quat | | |
| 75ppm dye | no quat | 225ppm quat | acid | neutral | alkaline | acid | neutral | alkaline |
| acid violet 148 | PURPLE | BLUE | PURPLE | PURPLE | PURPLE | BLUE | BLUE | BLUE |
| bromothymol blue | PURPLE | BLUE | PURPLE | PURPLE | PURPLE | BLUE | BLUE | BLUE |
| acid orange 7 | ORANGE | ORANGE | LIGHT ORANGE | ORANGE | ORANGE | LIGHT ORANGE | ORANGE | ORANGE |
| acid green 1 | GREEN | GREEN | LIGHT GREEN | GREEN | GREEN | LIGHT GREEN | GREEN | GREEN |
| acid yellow 36 | YELLOW | YELLOW | BROWN | YELLOW | YELLOW | BROWN | YELLOW | YELLOW |
| acid red 52 | RED | RED | PINK | RED | RED | PINK | RED | RED |
| methylene blue | BLUE | BLUE | LIGHT BLUE | BLUE | BLUE | LIGHT BLUE | BLUE | BLUE |
| alkali purple | PURPLE | BLUE | PURPLE | PURPLE | PURPLE | BLUE | BLUE | BLUE |

Related U.S. Application Data

(60) Provisional application No. 61/532,797, filed on Sep. 9, 2011.

(51) Int. Cl.
 *B65D 79/02* (2006.01)
 *B65D 81/28* (2006.01)

(56) References Cited

U.S. PATENT DOCUMENTS

| | | |
|---|---|---|
| 3,899,295 A | 8/1975 | Halpern |
| 3,963,442 A | 6/1976 | Bullard et al. |
| 4,180,009 A | 12/1979 | Voss et al. |
| 4,824,827 A | 4/1989 | Kelly et al. |
| 4,965,063 A | 10/1990 | Casey et al. |
| 5,057,303 A | 10/1991 | Casey |
| 5,064,635 A | 11/1991 | Casey |
| 5,110,492 A | 5/1992 | Casey |
| 5,254,473 A * | 10/1993 | Patel .................. G01N 31/229 116/216 |
| 5,710,372 A | 1/1998 | Becket |
| 5,869,341 A | 2/1999 | Woodaman |
| 6,378,906 B1 | 4/2002 | Pennaz |
| 6,557,484 B1 | 5/2003 | Engelman |
| 7,850,911 B2 | 12/2010 | Herrlein et al. |
| 8,754,146 B2 | 6/2014 | Ziolkowski et al. |
| 2003/0019954 A1 | 1/2003 | Clarke |
| 2006/0293205 A1 | 12/2006 | Chung |
| 2007/0117172 A1 | 5/2007 | Price et al. |
| 2007/0237807 A1 | 10/2007 | Luu et al. |
| 2008/0081020 A1 | 4/2008 | Huang et al. |
| 2008/0242569 A1 | 10/2008 | Carter et al. |
| 2009/0184081 A1 | 7/2009 | Wu et al. |
| 2010/0197027 A1 | 8/2010 | Zhang et al. |
| 2010/0221193 A1 | 9/2010 | Huang et al. |
| 2010/0240134 A1 | 9/2010 | Liner |
| 2010/0247371 A1 | 9/2010 | Farrugia et al. |
| 2013/0323854 A1 | 12/2013 | Kraus et al. |
| 2014/0242195 A1 | 8/2014 | Dixon |

FOREIGN PATENT DOCUMENTS

| | | |
|---|---|---|
| JP | 2004359319 A | 12/2004 |
| WO | WO 9919232 A2 | 4/1999 |
| WO | WO 2010085755 A1 | 7/2010 |

* cited by examiner

Color Change of Dyes with Addition of Quaternary Ammonium Compound Under Various pH Conditions

| | Initial Screen | | Effect of pH on Screening Solutions (diluted to 75% original conc.) | | | | | |
|---|---|---|---|---|---|---|---|---|
| | pH 7-8 | | no quat | | | with quat | | |
| 75ppm dye | no quat | 225ppm quat | acid | neutral | alkaline | acid | neutral | alkaline |
| acid violet 148 | PURPLE | BLUE | PURPLE | PURPLE | PURPLE | BLUE | BLUE | BLUE |
| bromothymol blue | PURPLE | BLUE | PURPLE | PURPLE | PURPLE | BLUE | BLUE | BLUE |
| acid orange 7 | ORANGE | ORANGE | LIGHT ORANGE | ORANGE | ORANGE | LIGHT ORANGE | ORANGE | ORANGE |
| acid green 1 | GREEN | GREEN | LIGHT GREEN | GREEN | GREEN | LIGHT GREEN | GREEN | GREEN |
| acid yellow 36 | YELLOW | YELLOW | BROWN | YELLOW | YELLOW | BROWN | YELLOW | YELLOW |
| acid red 52 | RED | RED | PINK | RED | RED | PINK | RED | RED |
| methylene blue | BLUE | BLUE | LIGHT BLUE | BLUE | BLUE | LIGHT BLUE | BLUE | BLUE |
| alkali purple | PURPLE | BLUE | PURPLE | PURPLE | PURPLE | BLUE | BLUE | BLUE | ered as U.S. Pat. No.
REAL TIME INDICATOR FOR QUATERNARY AMMONIUM COMPOUND CONCENTRATION

CROSS REFERENCE TO RELATED APPLICATIONS

This application is a continuation of application Ser. No. 13/605,862, filed Sep. 6, 2012, and issued as U.S. Pat. No. 9,144,620 on Sep. 19, 2013, which claims benefit of Provisional Application No. 61/532,797, filed Sep. 9, 2011, which applications are incorporated herein by reference.

BACKGROUND

Maintaining adequate levels of antimicrobial concentration is necessary to ensure that an antimicrobial solution is effective at reducing microorganisms. This is important in areas that are sensitive to microorganisms like the food service or healthcare industries where microorganisms can cause food spoilage, illness, or infection. Frequently replacing an antimicrobial solution is one way to maintain the antimicrobial concentration. But, this may result in wasting active antimicrobial solution.

SUMMARY

The present disclosure generally relates to a color indicator that signals when the concentration of an antimicrobial solution changes.

In some aspects, the disclosure relates to a color changing plastic container having a color changing dye incorporated into the substance of the container itself where the dye imparts a color to the container such that the container is a first color if the concentration of a quaternary ammonium compound is above a threshold and a second color if the concentration of the quaternary ammonium compound is below the threshold.

In some aspects, the disclosure relates to a method of monitoring the concentration of quaternary ammonium compound solution in a container. The container has a color changing dye incorporated into its structure, where the dye imparts a color to the container such that the container is a first color if the concentration of the quaternary ammonium compound is above a threshold, for example, 100 ppm, and a second color if the concentration of the quaternary ammonium compound is below a threshold, for example, 100 ppm. The method includes adding a quaternary ammonium compound antimicrobial solution to the container, using the quaternary ammonium solution for a period of time and adding quaternary ammonium solution to the container in response to the container color changing from the first color to the second color.

In some aspects, the disclosure relates to a color changing label that has a substrate and a color changing dye that changes color if the concentration of a quaternary ammonium compound is above a threshold and a second color if the concentration of the quaternary ammonium compound is below the threshold.

In some aspects, the disclosure relates to a method of monitoring the concentration of quaternary ammonium compound in a container using a color changing label. The label includes a substrate and a color changing dye that changes color if the concentration of a quaternary ammonium compound is above a threshold and a second color if the concentration of the quaternary ammonium compound is below the threshold. The method includes applying a label to a container where the label is placed on the container in such a way that the label will contact any solution that is placed in the container, adding a quaternary ammonium compound antimicrobial solution to the container, using the quaternary ammonium solution for a period of time, and adding quaternary ammonium solution to the container in response to the label changing color from the first color to the second color.

In some aspects, the disclosure relates to a color changing article with a substrate and a color changing dye that changes color if the concentration of a quaternary ammonium compound is above a threshold and a second color if the concentration of the quaternary ammonium compound is below the threshold.

In some aspects, the disclosure relates to a method of monitoring the concentration of quaternary ammonium compound in a container using a color changing article. The article includes a substrate and a color changing dye that changes color if the concentration of a quaternary ammonium compound is above a threshold and a second color if the concentration of the quaternary ammonium compound is below the threshold. The method includes adding a quaternary ammonium compound antimicrobial solution to the container, using the quaternary ammonium solution for a period of time, placing an article into the quaternary ammonium solution, and adding quaternary ammonium solution to the container in response to the article color being the second color.

BRIEF DESCRIPTION OF THE DRAWINGS

The present disclosure is further described with reference to the appended FIGURE.

FIG. 1 shows the color change of dyes with the addition of quaternary ammonium compound under various pH conditions.

DETAILED DESCRIPTION

The present disclosure generally relates to a color indicator that signals when the concentration of an antimicrobial solution changes. In some embodiments, the color indicator is specific for changes in the concentration of an antimicrobial quaternary ammonium compound in an antimicrobial solution. The color indicator includes a dye. The dye is preferably pH stable, meaning that the color change associated with the change in antimicrobial concentration is independent of the pH of the antimicrobial solution. Put another way, the dye preferably performs the same if the antimicrobial solution is at an acidic, neutral, or basic pH. This is in contrast to pH indicator dyes that are specifically designed to change color as the pH changes. In some embodiments, the dye is reversible in that once it changes from a first color to a second color, it can also change from the second color back to the first color. This is in contrast to indicator dyes, such as on quaternary ammonium test strips, that do not change back to their original color once they have changed color.

In some embodiments, the color change is triggered by a change in quaternary ammonium compound concentration in a solution where the color changes as the concentration passes a certain threshold. In some embodiments, the concentration threshold is the point where the antimicrobial solution goes from being an effective antimicrobial solution to not being an effective antimicrobial solution. For example, for some applications, the antimicrobial solution preferably includes at least about 100, 150, or 200 ppm of quaternary ammonium compound for the overall solution to be effective at reducing the presence of microorganisms. For other applications, the antimicrobial solution preferably includes at least about 600, 800, 1000, or 2000 ppm of quaternary ammonium compound for the overall solution to be effective at reducing the presence of microorganisms. Therefore, in some embodiments, the disclosed dye changes color as the concentration drops under 100, 150, 200, 300, 400, 500, 600, 700, 800, 900, 1000, 1500, or 2000 ppm quaternary ammonium compound. In some embodiments, the color changes before the quaternary ammonium compound drops the threshold to signal that the concentration of quaternary ammonium compound is getting close to being low. For example, in may be desirable for the color change to happen at least 100 ppm before the concentration of quaternary ammonium compound drops under the threshold, i.e., 200, 250, 300, 700, 900, 1100, or 2100 ppm if using some of the above stated thresholds. In some embodiments, it may be desirable for the color change to be gradual as the concentration nears the threshold and complete once the concentration reaches threshold quaternary ammonium compound concentration. In some embodiments, the color change may be multicolored where the color changes from a first color to a second color as the concentration nears a first threshold (such as a warning threshold), and then the color changes from the second color to the third color once the concentration reaches a second threshold (such as the point where the solution is no longer an effective antimicrobial solution). In some embodiments, the color change is arbitrary and not linked to the effectiveness of the solution. In such embodiments, the color change serves as a reminder to replace the antimicrobial solution before the solution stops being effective. In some embodiments, the color change can be triggered by a time lapse and not the quaternary ammonium concentration.

In some embodiments, the "color change" includes a change from no color to color, or color to no color. For example, in some embodiments, the "color change" can include words or symbols appearing where words or symbols were not previously there or were a different color. Alternatively, a container may go from clear or colorless to colored, or white to colored or vice versa (colored to clear/colorless or colored to white) for the "color change."

In some embodiments, it may be desirable for the color change to include words, phrases, instructions, or graphics for the user to check the concentration of the antimicrobial solution. For example, when the dye is part of a label, the color change can include a word or phrase appearing on the label such as: "CHANGE", "REPLACE", "QUAT", "IT IS TIME TO CHANGE THE SOLUTION", "NO QUAT" and the like. Alternatively, the color change can also include a word or phrase disappearing such as: "QUAT", "ANTIMICROBIAL" and the like.

In some embodiments, the "color change" can occur outside of the visible range of colors. In other words, an indicator can be used that changes color from a first wavelength to a second wavelength outside of the visible range such as the infrared spectrum or the ultraviolet spectrum. Additionally, the "color change" can be such that, even in the visible range, the change in color is too slight to perceive visually, but can nevertheless be quantified by instrumentation. Therefore, in such embodiments where the color change is not perceptible to the eye or occurs outside of the visible range, a sensor can be used to measure the change. Exemplary sensors include color (RBG) sensors that measure the color or wavelength of a substrate such as a test strip, coupon, tag, container, article, or the like. Such a sensor could be found in a "pen"- or "flashlight"-like article that a user flashes at the substrate. The sensor could also be integral with the container such that the sensor provides a constant or periodic reading of the quaternary ammonium compound concentration in the container. In such embodiments, the sensor can optionally include a word, light or sound alarm or warning that alerts a user that the concentration of quaternary ammonium compound may need to be adjusted or replaced. The sensor may optionally include a transmitter and receiver such as in a wireless device that would be able to identify a remote solution as being near or below a threshold and send a signal to a location (such as a computer terminal) that would alert a user that the solution needs to be adjusted or replaced. In some embodiments, the dye can be immobilized on a clear (plastic or glass) indicator wand together with a sensor. The wand can be configured in such a way that the sensor is located on the "back" or "dry" side of the wand and when the opposing or "wet" side of the wand is inserted into a quaternary ammonium compound or solution, the dye on the wet side would change color and that color change would be measurable by the sensor.

Exemplary color changing dyes include dyes that are pH independent and pH stable and that exhibit a first color when the concentration of quaternary ammonium compound is above a threshold and a second color when the concentration of quaternary ammonium compound is below a threshold. Preferred dyes are reversible in that once they change color, they can change back to their original color. Preferred color changing dyes have been found to be purple where the purple is a true purple and not simply a combination of red and blue dyes. Prefered color change dyes are anionic. Exemplary dyes include Acid Violet 148, bromothymol blue, and alkali purple. Notably, the name of the dye is not indicative of its properties. For example, bromothymol blue is actually purple and not blue. In an embodiment, the dye is not bromothymol blue. One particularly preferred dye includes Acid Violet 148, commercially available from KeyColour, which is purple in the presence of quaternary ammonium compound and blue in the absence or reduced presence of quaternary ammonium compound. This dye changes color in real time and is independent of the pH of the antimicrobial solution.

The color changing dyes can be incorporated into a variety of articles such as towels, labels, containers, buckets, trays, sinks, spray bottles, liners for containers, buckets, sinks, or spray bottles, indictor wands or strips, and test kits. Regarding the label, the dye can be incorporated into the label substrate itself or into the ink that gets printed onto the substrate. The dye can also be incorporated into the material that forms the article, such as the plastic that forms a plastic container, or the yarn that forms fabric. For example, when synthetic textiles are made, the process starts with resin pellets that are extruded to make fine filaments. The dye can be incorporated into the resin and then extruded to form the filaments. Thus the dye will be integral with the fiber that goes on to form thread and eventually a woven or nonwoven textile. The dye can also be incorporated into a paint and then painted onto the article.

Exemplary plastics include high density polyethylene, low density polyethylene, linear low density polyethylene, ethylene vinyl acetate, ethylene methyl acrylate, ethylene acrylic acid, ethylene methacrylic acid, polypropylene, nylon, PET, PVC (polyvinyl chloride), PVdC, EVOH, polyurethane, Barex, polystyrene, and combinations thereof. The concentration of the dye can be increased or decreased to change at a higher or lower concentration of quaternary ammonium compound. A sub-stoichiometric concentration of dye to quaternary ammonium compound has been found to be sufficient for creating the necessary color change.

In some embodiments, it is advantageous for the color change be passive to the observer, meaning that the user or observer does not need to perform a specific activity such as putting a test strip into the solution in order to see the color change. Examples of this include a color changing container that changes color as the quaternary ammonium concentration changes.

For a more complete understanding of the articles and methods, the following examples are given to illustrate some embodiments. These examples and experiments are understood as illustrative and not limiting. All parts are by weight, except where it is contrarily indicated.

EXAMPLES

Example 1

Solutions of 75 ppm dye with and without 225 ppm quaternary ammonium compound (Bardac 205 from Lonza) were prepared and adjusted to an acid pH with 5% HCl or an alkaline pH with 5% NaOH or allowed to remain in their initial neutral pH. Those solutions were then treated with 75 ppm Acid Violet 148 dye (available from KeyColour) and the color of the various solutions noted. As the data in FIG. 1 illustrate, and in particular, the leftmost grouping of data, the color change from the interaction of quat and dye was noted only for purple and/or violet dyes. As shown in the middle and rightmost grouping of data, this color change remained essentially the same, regardless of pH. Other colors of dye (blue, green, red, yellow, orange) did not result in any color change when quaternary ammonium compound was added.

Example 2

A spatula tip of Acid Violet 148 was mixed with a white enamel paint which was then used to coat a coupon of plastic with a white coating. After drying, a section of the plastic panel was exposed to a 400 ppm solution of quaternary ammonium compound, forming an intense purple color. When treated with water, but no quaternary ammonium compound, a section of the white panel turned blue. When treated with about 150 ppm of quaternary ammonium compound, a second of the white panel turned a pale purple. When the section previously treated with 150 ppm of quaternary ammonium compound was treated with 400 ppm quaternary ammonium compound, it turned an intense purple.

The plastic coupon was then rinsed well with water and allowed to dry. All treated areas reverted to white. The spots previously treated with 400 ppm of quaternary ammonium compound were once again treated with 400 ppm quaternary ammonium compound, resulting in the formation of the intense purple color again. This demonstrates that the color change is reversible.

The above specification, examples and data provide a complete description of the manufacture and use of the present disclosure. Since many embodiments can be made without departing from the spirit and scope of the disclosure, the invention resides in the claims.

We claim:

1. A method of monitoring the concentration of quaternary ammonium compound in a container comprising:
   (a) applying a label to a container, wherein the label is placed on the container in such a way that the label will contact any solution that is placed in the container, wherein the label comprises:
      (i) a substrate; and
      (ii) a pH stable dye located on the substrate that exhibits a first color when in contact with an antimicrobial quaternary ammonium compound at a concentration that is above a threshold, and a second color when in contact with the antimicrobial quaternary ammonium compound at a concentration that is below the threshold, the color change from the first color to the second color being reversible and can occur more than once, the pH stable dye selected from the group comprising Acid Violet 148, alkali purple, or a mixture thereof;
   (b) adding to the container a solution comprising an antimicrobial quaternary ammonium compound at a concentration that is above the threshold;
   (c) using the solution for a period of time; and
   (d) monitoring the concentration of the antimicrobial quaternary ammonium compound by observing the color of the label.

2. The method of claim 1 further comprising:
   (e) adding additional antimicrobial quaternary ammonium compound to the container in response to the label changing color from the first color to the second color.

3. The method of claim 1, wherein the label displays a word or a phrase when the pH stable dye exhibits the second color to indicate a need to replenish the antimicrobial quaternary ammonium compound solution.

4. The method of claim 1, wherein the threshold concentration is 100 ppm quaternary ammonium compound.

5. The method of claim 1, wherein the container comprises a bucket, a sink, or a bottle.

6. A method for monitoring quaternary ammonium compound level in a solution, the method comprising:
   (a) applying a solution to an article, wherein the solution comprises a quaternary ammonium compound;
   (b) observing an indicator on the article,
   wherein the indicator comprises a pH stable dye that exhibits a first color when in contact with a first concentration of the quaternary ammonium compound that is above a threshold, and a second color when in contact with a second concentration of the quaternary ammonium compound that is below the threshold, the pH stable dye selected from the group comprising Acid Violet 148, alkali purple, or a mixture thereof
   wherein the indicator is capable of reversibly changing color.

7. The method of claim 6, wherein the indicator is part of a label affixed to the article by an adhesive.

8. The method of claim 7, wherein the dye forms text or a symbol on a front surface of the label indicating a need to add more of the quaternary ammonium compound or to change or replenish the solution.

9. The method of claim 6, wherein the threshold is 100 ppm of the quaternary ammonium compound.

10. The method of claim 6, wherein the indicator is observed visually.

11. The method of claim 6, wherein the indicator is observed using a sensor.

12. The method of claim 11, wherein the sensor comprises a color sensor that measures a wavelength.

13. The method of claim 11, wherein the sensor is integral with the article.

14. The method of claim 11, wherein the sensor gives out a light or sound alarm when the sensor detects the second color.

15. The method of claim 6, wherein the article comprises a towel, a label, a container, a bucket, a sink, a bottle, or an indicator wand.

\* \* \* \* \*

UNITED STATES PATENT AND TRADEMARK OFFICE
CERTIFICATE OF CORRECTION

PATENT NO. : 10,514,367 B2
APPLICATION NO. : 14/835096
DATED : December 24, 2019
INVENTOR(S) : Balz et al.

Page 1 of 1

It is certified that error appears in the above-identified patent and that said Letters Patent is hereby corrected as shown below:

In the Specification

Column 1, Line 10: "9,144,620 on Sep. 19, 2013," should read --9,144,620 on Sep. 29, 2015,--

Signed and Sealed this
Fifth Day of January, 2021

Andrei Iancu
*Director of the United States Patent and Trademark Office*